(12) United States Patent
Larson et al.

(10) Patent No.: US 9,101,344 B2
(45) Date of Patent: Aug. 11, 2015

(54) RECIRCULATING COOLING SYSTEM FOR ENERGY DELIVERY DEVICE

(71) Applicant: Covidien LP, Mansfield, MA (US)

(72) Inventors: Eric W. Larson, Thornton, CO (US); Darion R. Peterson, Boulder, CO (US); Joseph D. Brannan, Erie, CO (US)

(73) Assignee: Covidien LP, Mansfield, MA (US)

( * ) Notice: Subject to any disclaimer, the term of this patent is extended or adjusted under 35 U.S.C. 154(b) by 228 days.

(21) Appl. No.: 13/835,625

(22) Filed: Mar. 15, 2013

(65) Prior Publication Data

US 2014/0276740 A1   Sep. 18, 2014

(51) Int. Cl.

| A61B 18/02 | (2006.01) |
|---|---|
| A61B 18/00 | (2006.01) |
| A61B 18/18 | (2006.01) |
| A61N 5/00 | (2006.01) |

(52) U.S. Cl.
CPC .............. *A61B 18/02* (2013.01); *A61B 18/00* (2013.01); *A61B 18/18* (2013.01); *A61B 2018/00023* (2013.01); *A61B 2018/00577* (2013.01); *A61B 2018/0262* (2013.01); *A61N 2005/005* (2013.01)

(58) Field of Classification Search
CPC .............. A61B 2018/0262; A61B 2018/00023
USPC .......................................... 606/33, 34, 41, 22
See application file for complete search history.

(56) References Cited

U.S. PATENT DOCUMENTS

| 5,545,161 | A | * | 8/1996 | Imran .............................. 606/41 |
|---|---|---|---|---|
| 6,478,793 | B1 | | 11/2002 | Cosman et al. |
| 6,506,189 | B1 | | 1/2003 | Rittman, III et al. |
| 6,514,251 | B1 | | 2/2003 | Ni et al. |
| 6,575,969 | B1 | | 6/2003 | Rittman, III et al. |
| 7,052,463 | B2 | | 5/2006 | Peszynski et al. |
| 8,292,880 | B2 | | 10/2012 | Prakash et al. |
| 8,334,812 | B2 | | 12/2012 | Brannan |
| 8,430,871 | B2 | | 4/2013 | Brannan |
| 2009/0149930 | A1 | | 6/2009 | Schenck |
| 2009/0222002 | A1 | | 9/2009 | Bonn et al. |
| 2010/0053015 | A1 | * | 3/2010 | Willyard ........................ 343/790 |

(Continued)

FOREIGN PATENT DOCUMENTS

| EP | 2 540 260 | | 1/2013 |
|---|---|---|---|
| EP | 2550924 | A1 | 1/2013 |
| KR | 101016566 | B1 | 2/2011 |
| WO | WO 2004/034940 | | 4/2004 |
| WO | WO 2011/056684 | | 5/2011 |

OTHER PUBLICATIONS

Partial European Search Report dated Jun. 3, 2014 issued in European Application No. 14159833.

(Continued)

*Primary Examiner* — Christopher D Koharski
*Assistant Examiner* — Michael Carey

(57) ABSTRACT

An energy delivery device cooling system includes a reservoir connector assembly and an elongate member. The elongate member has first and second lumens in fluid communication with the reservoir. The first lumen includes an outflow port and the second lumen includes a return port each in fluid communication with the reservoir. The device further includes a tubing system having a first end and a second end. The first end connected in fluid communication with the outflow port and the second end in fluid communication with the return port. The second end configured to return a fluid to the reservoir. The tubing system connects to an energy delivery device to cool the fluid.

21 Claims, 7 Drawing Sheets

(56) References Cited

U.S. PATENT DOCUMENTS

| | | |
|---|---|---|
| 2010/0057074 A1 | 3/2010 | Roman et al. |
| 2010/0228162 A1 | 9/2010 | Sliwa et al. |
| 2011/0077637 A1* | 3/2011 | Brannan ............... 606/33 |
| 2011/0118724 A1 | 5/2011 | Turner et al. |
| 2011/0295245 A1 | 12/2011 | Willyard et al. |
| 2013/0030426 A1* | 1/2013 | Gallardo et al. ............ 606/33 |

OTHER PUBLICATIONS

U.S. Appl. No. 13/835,808, filed Mar. 15, 2013, Larson et al.
U.S. Appl. No. 13/838,805, filed Mar. 15, 2013, Baker.
U.S. Appl. No. 13/838,203, filed Mar. 15, 2013, Ladtkow et al.
European Search Report dated Oct. 1, 2014 issued in European Appln. No. 14 15 9833.

* cited by examiner

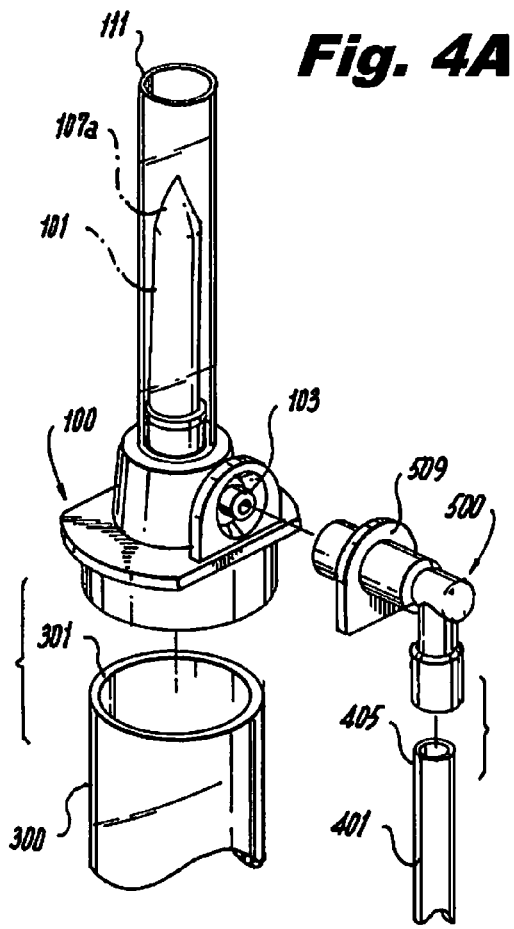
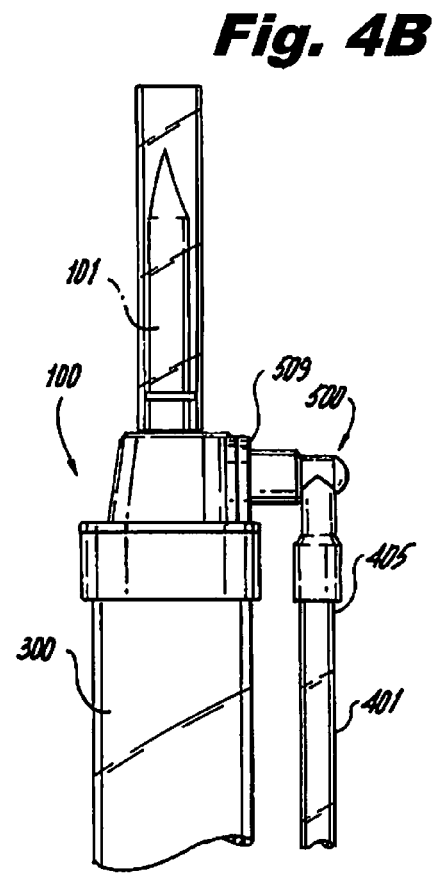
Fig. 4A   Fig. 4B
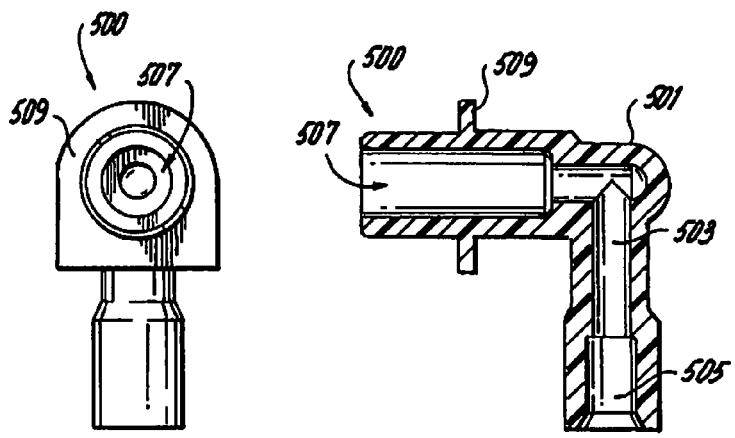
Fig. 5A   Fig. 5B   Fig. 5C

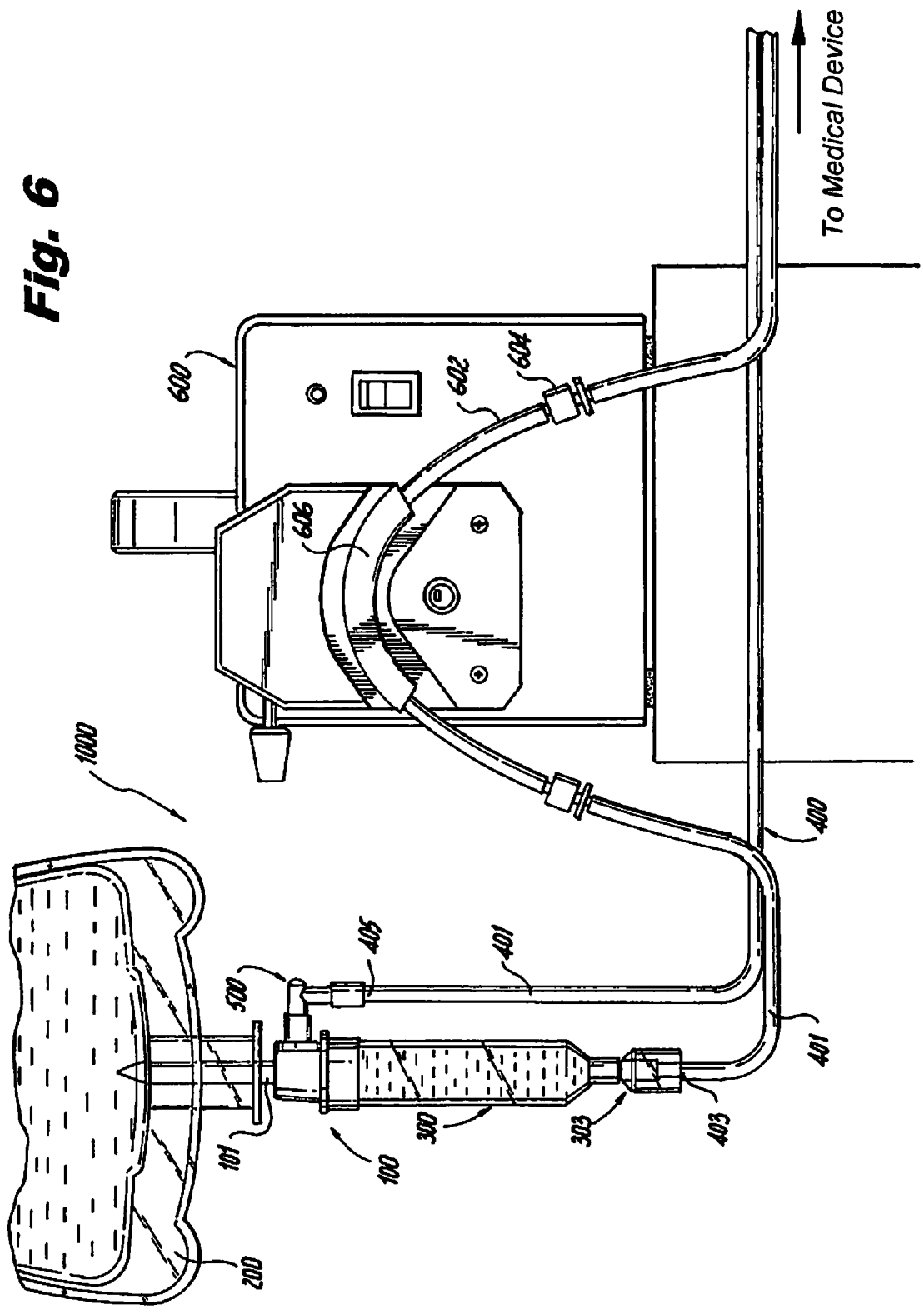

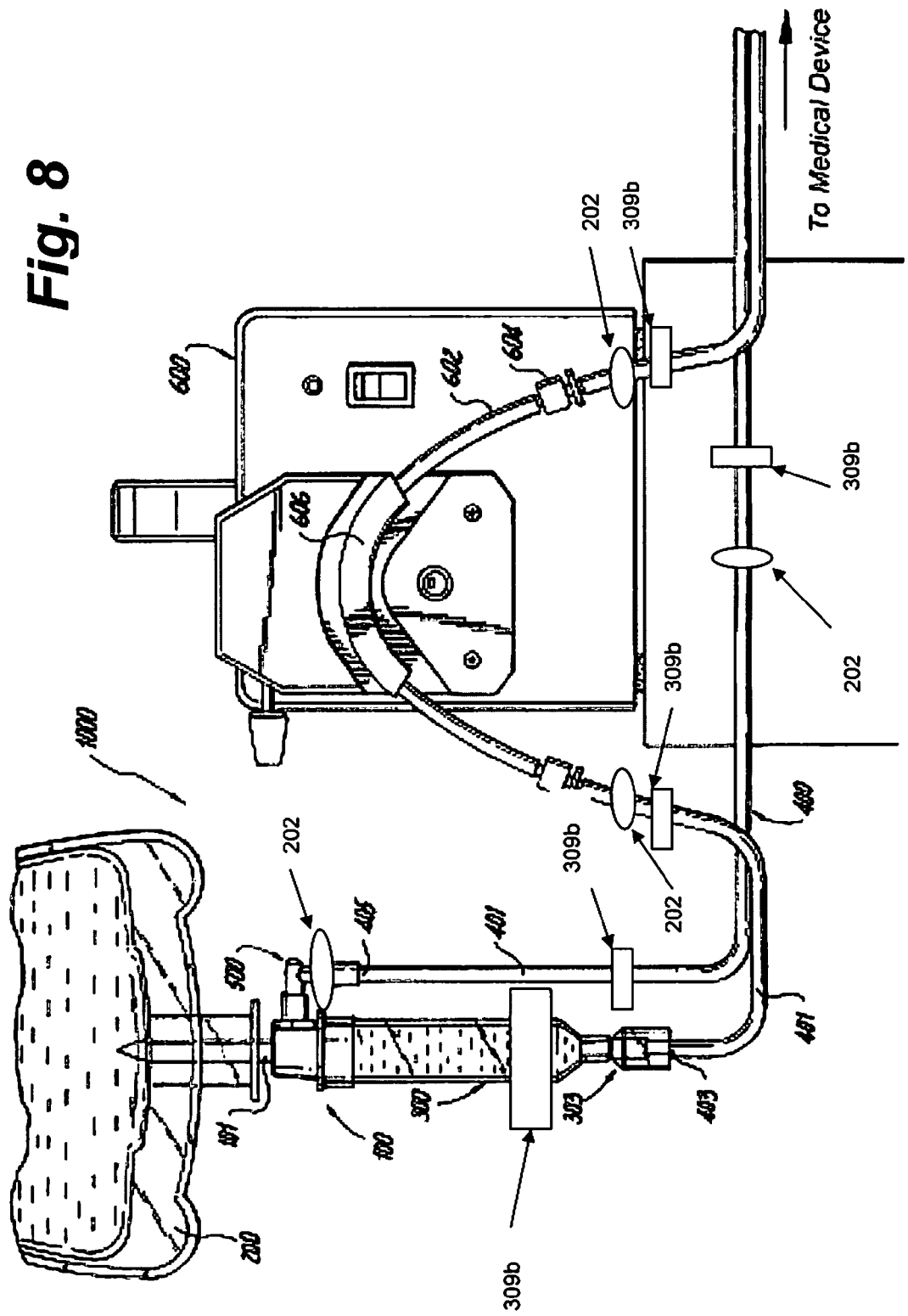

RECIRCULATING COOLING SYSTEM FOR ENERGY DELIVERY DEVICE

BACKGROUND

1. Technical Field

The present disclosure relates to the use of energy delivery devices. More particularly, the present disclosure is directed to cooling systems for energy delivery devices.

2. Background of the Related Art

Energy delivery procedures such as tissue ablation are used in numerous medical procedures to treat many conditions. Ablation can be performed to remove undesired tissue such as cancer cells. Ablation procedures may also involve the modification of the tissue without removal, such as to stop electrical propagation through the tissue in patients with an arrhythmia condition. Often the ablation is performed by passing energy, such as electrical energy, through one or more electrodes and causing the tissue in contact with the electrodes to heat up to an ablative temperature.

Electromagnetic (EM) ablation may also be used instead of direct energy discharge into tissue. For example, microwave (MW) ablation is a common example of such EM ablation where energy is applied to tissue through microwave radiation. EM ablation devices may require cooling to operate within desired parameters without damaging the ablation device or causing unintended tissue damage. Examples of EM ablation medical devices include percutaneous needle ablation probes and flexible intraluminal ablation catheters. Some devices implement cooling systems including a peristaltic pump that forces saline or another fluid through a tubing system operably connected to an energy delivery device. The saline solution draws heat from the energy delivery device and is then pumped out into a receptacle or to a drain. However, these systems require constant supply of saline bags, can be wasteful, and can be inefficient.

SUMMARY

Like reference numerals may refer to similar or identical elements throughout the description of the figures. As shown in the drawings and described throughout the following description, as is traditional when referring to relative positioning on a surgical instrument, the term "proximal" refers to the end of the apparatus that is closer to the user and the term "distal" refers to the end of the apparatus that is farther away from the user. The term "clinician" refers to any medical professional (e.g., doctor, surgeon, nurse, or the like) performing a medical procedure involving the use of embodiments described herein.

One aspect of the present disclosure is directed to a medical device cooling system including a reservoir connector assembly connectable to a reservoir and a tubing system. The reservoir connector assembly including an elongate member, an outflow port, and a return port. The elongate member extends into the reservoir. The elongate member has a first lumen in fluid communication with the reservoir and the outflow port and has a second lumen in fluid communication with the reservoir and the return port. The tubing system has a first end in fluid communication with the reservoir through the outflow port and a second end in fluid commutation with the reservoir through the return port. The tubing system is configured to cool the medical device. The elongate member may include a third lumen and a fourth lumen. Each of the third and fourth lumens in fluid communication with the reservoir through outflow ports.

In embodiments, the system includes a pump configured to pressurize a fluid in the tubing system. The pump may be a peristaltic pump.

According to a further aspect of the present disclosure, the system includes a drip chamber connected downstream of the outflow port. In embodiments, the drip chamber may include a fluid flow indicator. The fluid flow indicator may be a rotating cylinder or a semi-buoyant spinning cube. The system may also include a thermal diffusion device configured to draw heat from the fluid and diffuse the heat to an ambient environment. The reservoir may be a saline bag. In some embodiments, the system includes an elbow member connected to and in between the second end of the tubing system and the return port of the reservoir.

Yet a further aspect of the present disclosure is directed to a fluid return elbow for use with medical device cooling systems. The elbow includes a body defining a lumen, an inflow port in fluid communication with the lumen, and an outflow port in fluid communication with the lumen. The inflow port is configured to connect to a return section of a fluid tubing system. The outflow port is configured to connect to a return port of a reservoir connection assembly. In embodiments, the elbow includes a flange disposed around the outflow port to ensure proper alignment of the elbow with a reservoir connection assembly. The inflow port of the elbow may be configured to connect to tubing of a cooling system for a medical device. The outflow port of the elbow may be configured to connect to a return port of an elongate member inserted in a fluid reservoir such as saline bag.

Still a further aspect of the present disclosure is directed to a system for cooling a medical ablation device. The system includes a fluid reservoir, a tubing system, a pump, a medical ablation device, and a fluid flow indicator. The fluid reservoir is configured to hold a cooling fluid. The tubing system connects the fluid reservoir to the medical device in fluid communication. The pump attaches to the tubing system and induces fluid flow from the fluid reservoir through the tubing system. The cooling fluid flows through the tubing system from the fluid reservoir and through the medical device before returning to the fluid reservoir. As the cooling fluid flows through the medical ablation device, the cooling fluid draws heat from the medical ablation device. The cooling fluid may be recirculated into the fluid reservoir and reused. In embodiments, the system includes at least one thermal diffusion device that facilitates thermal diffusion from the cooling fluid to the environment. The fluid flow indicator provides visual indicia of cooling fluid flow through the system. The fluid flow indicator may be a bubble indicator, a venturi device, a drip chamber indicator, a float type indicator, a hall-effect indicator, or an electromagnetic indicator.

BRIEF DESCRIPTION OF THE DRAWINGS

The above and other aspects, features, and advantages of the present disclosure will become more apparent in light of the following detailed description when taken in conjunction with the accompanying drawings in which:

FIG. 4A is an exploded view of a portion of the cooling system in accordance with the present disclosure;

FIG. 4B is a side view of the portion of the cooling system of FIG. 4A;

FIG. 5A is a cross-sectional view of a fluid return elbow member in accordance with the present disclosure;

FIG. 5B is a front view of the fluid return elbow of FIG. 5A;

FIG. 5C is a bottom view of the fluid return elbow of FIG. 5A;

FIG. 6 is a side view of a cooling system in accordance with the present disclosure;

FIG. 8 is a side view of a cooling system in accordance with the present disclosure depicting locations of flow sensors and thermocouples.

DETAILED DESCRIPTION

Particular embodiments of the present disclosure are described hereinbelow with reference to the accompanying drawings; however, the disclosed embodiments are merely examples of the disclosure and may be embodied in various forms. Well known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In accordance with at least one aspect of the present disclosure, an energy delivery device cooling system is disclosed. Referring generally to FIGS. 1-6, the system 1000 includes a reservoir connector assembly 100 in communication with a reservoir 200. The reservoir 200 is configured to contain or hold a cooling fluid. The reservoir connector assembly 100 may include an elongate member 101 configured to extend into the reservoir 200. Tubing system 400 connects the reservoir 200 with a medical device having inlet and outlet ports and forming a closed loop cooling system 1000, as will be described in greater detail below. Examples of medical devices to which the system 1000 may be connected can be found in commonly owned U.S. Pat. No. 8,334,812, U.S. patent application Ser. No. 12/607,221, filed Oct. 28, 2009, and now published as U.S. patent application No. 2011/0098696, U.S. patent application Ser. No. 13/838,805, filed Mar. 15, 2013, and now published as U.S. Patent Publication No. 2014/0281961, and U.S. patent application Ser. No. 13/836,203, filed Mar. 15, 2013, and now published as U.S. Patent Publication No. 2014/0046315, each of which is incorporated herein by reference in its entirety.

In some embodiments, the elongate member 101 can have any length and shape capable of being inserted into the reservoir 200. For example, the elongate member 101 can be a spike with a penetrating tip. In other embodiments, the elongate member 101 can have a blunt or substantially flat tip. The elongate member 101 can be substantially cylindrical, and in the embodiments with a piercing tip, the tip can be symmetrically conical or non-symmetrically conical.

Figure 1:
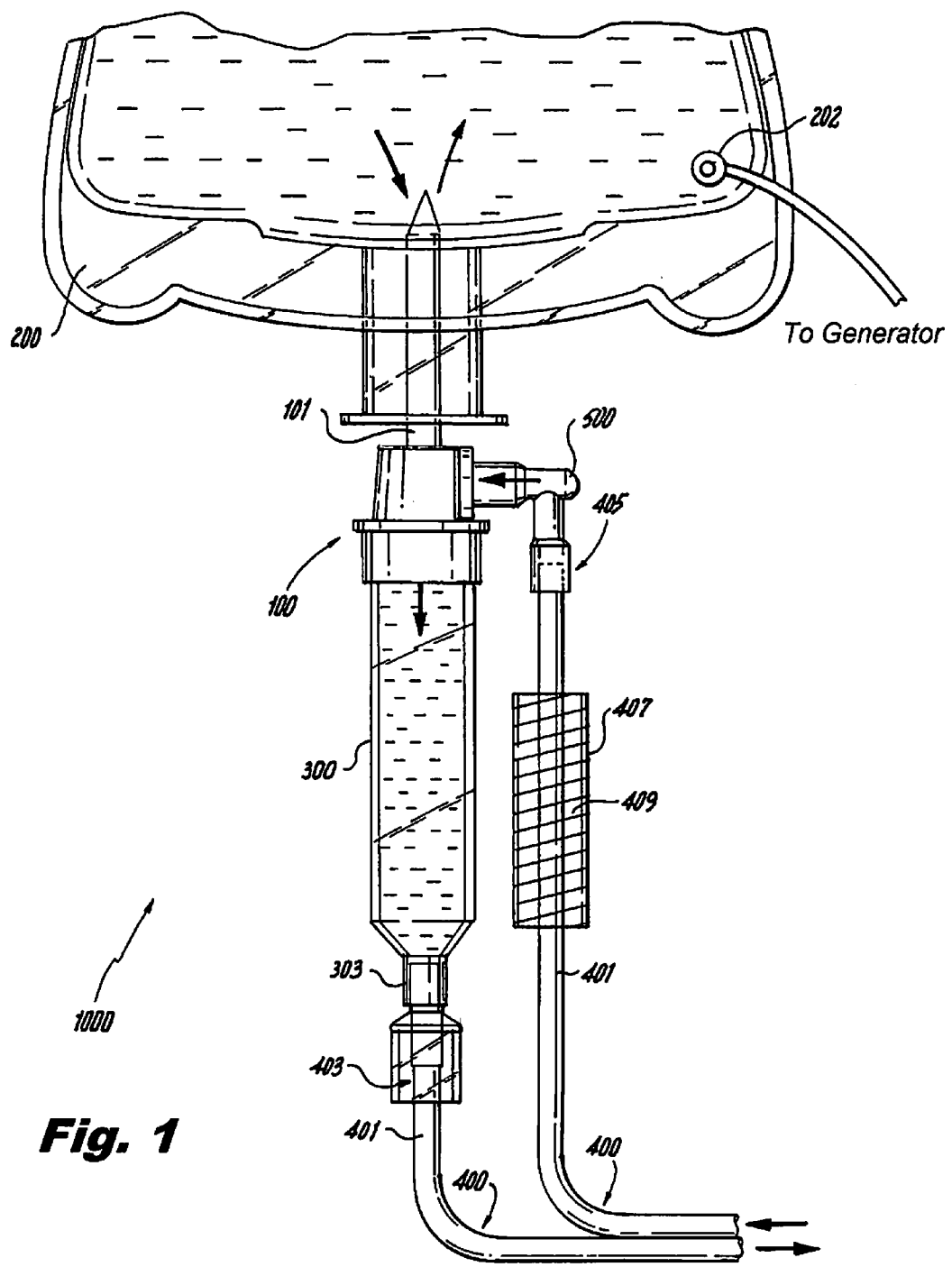
FIG. 1 is a side view of a portion of a cooling system in accordance with the present disclosure.
Figure 2:
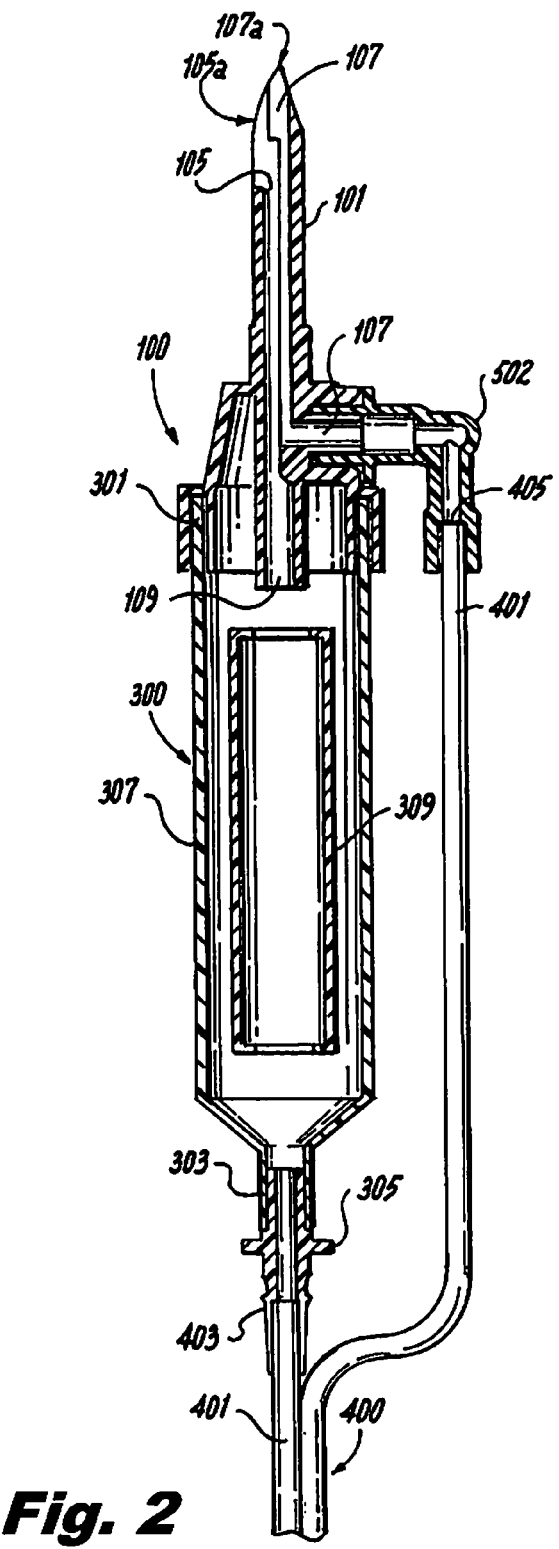
FIG. 2 is a cross-sectional view of a drip chamber and flow indicator, in accordance with the present disclosure.

Referring specifically to FIG. 2, the elongate member 101 has at least a first lumen 105 and a second lumen 107 defined therethrough. Each lumen 105, 107 is configured to be in fluid communication with the reservoir 200 shown in FIG. 1 at openings 105a and 107a respectively. The first lumen 105 may act as an inflow lumen for drawing fluid from the reservoir 200 and the second lumen 107 may act as a return lumen for returning fluid to the reservoir 200.

Lumens 105, 107 and openings 105a, 107a may have the same or different diameters. The diameter of the lumens 105, 107 may be selected based on a desired volumetric flow rate and fluid velocity for a given medical device. For example, to promote mixing in the reservoir 200, a smaller diameter lumen 107 can be chosen to achieve a higher velocity of the fluid for a given pressure. The increased velocity can increase turbulent flow within the reservoir 200 and/or the tubing system 400, resulting in increased mixing of the fluid. This increased mixing can promote homogenization of the fluid temperature within the reservoir 200 and/or the tubing system 400. The turbulent flow can also increase the efficiency of the transfer of heat from the fluid to the surrounding environment.

At least one outflow port 109 is in fluid communication with the first lumen 105 and allows fluid to flow from the reservoir 200 into a drip chamber 300 or directly into the tubing system 400. With continued reference to FIG. 2 and added reference to FIG. 4A, the reservoir connector assembly 100 includes a return port 103 configured to allow cooling fluid to return to the reservoir connector assembly 100 from the tubing system 400. The return port 103 is in fluid communication with the second lumen 107 and may be configured to allow for direct or indirect fluid communication with tubing system 400. It is also envisioned that the reservoir connector assembly 100 includes more than one return port 103.

In some embodiments, the elongate member 101 further includes a third lumen and a fourth lumen having third and fourth openings, respectively, and in fluid communication with the reservoir 200 and the outflow port 109. Similarly, added lumens may also connect to the return port 103.

The elongate member 101 or the reservoir 200 may include a thermocouple 202 operably connected thereto to monitor a temperature of the fluid inside the reservoir 200. Alternatively, the thermocouple 202 may be placed in various locations to measure the temperature of the fluid in the system 1000, as shown in FIG. 8. For example, the thermocouple 202 may be placed near the opening of the second lumen 107 to measure the temperature of the fluid flowing into the reservoir 200, near the first lumen 105 to measure the temperature of the fluid flowing out of the reservoir 200, in a portion of the tubing system 400 to measure the temperature of fluid flowing therein, or any combination thereof. The thermocouple 202 may be connected to an energy source for the medical device, for example a microwave generator (not shown), and may be employed as a safety shut off for the energy source such that if the temperature of the fluid rises beyond a set threshold that indicates insufficient cooling, the energy source is shut off to prevent undesired damage to patient tissue during treatment.

As shown in FIG. 1, a reservoir connector assembly 100 fluidly connects the reservoir 200 with a drip chamber 300. The drip chamber 300 may include a top portion 301 (FIG. 4A) configured to receive a portion of the reservoir connector assembly 100 and a bottom portion 303 configured to connect the drip chamber 300 in fluid communication with the tubing system 400. In embodiments, a fluid connector 305 connects the bottom portion 303 with the tubing system 400 and facilitates fluid communication therebetween. Between the top portion 301 and the bottom portion 303 is a central portion 307, which may be formed as a cylinder. As shown in FIGS. 2, 7, and 8, the central portion 307 of the drip chamber 300 may also include a flow indicator 309 for indicating that a fluid is flowing from the reservoir 200 through the drip chamber 300 to the tubing system 400.

Figure 3:
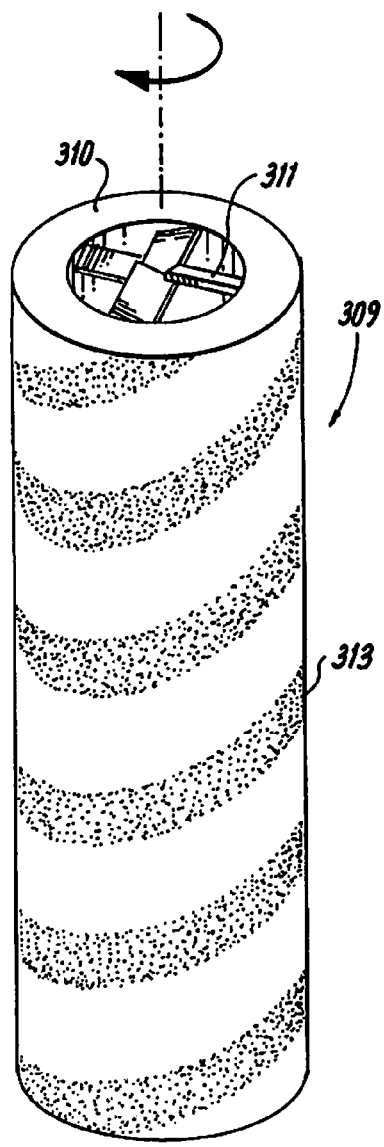
FIG. 3 is a perspective view of a flow indicator of a cooling system in accordance with the present disclosure.

As shown in FIG. 3, the flow indicator 309 may be formed of a hollow cylinder 310 with hydrofoils 311 configured to rotate the hollow cylinder 310 in the drip chamber 300 when fluid flows through the flow indicator 309. The flow indicator 309 may include a design 313 disposed on an outer surface thereof that visually indicates that the cylinder 309 is rotating, and thus that fluid is flowing therethrough. For example, the design 313 may resemble a barber-shop pole, however, other designs can be used to indicate fluid flow, for example a corporate logo COVIDIEN® or other graphic design. The cylinder 310 may be formed of a material with a specific gravity causing the cylinder 310 to either be neutrally buoyant in the cooling fluid or to float in the cooling fluid. Other embodiments of flow indicators 309 may be utilized that are suitable for indicating flow in the drip chamber 300 including but not limited to low density balls, floating material indicators, paddle wheel indicators, or the like.

Figure 7A:
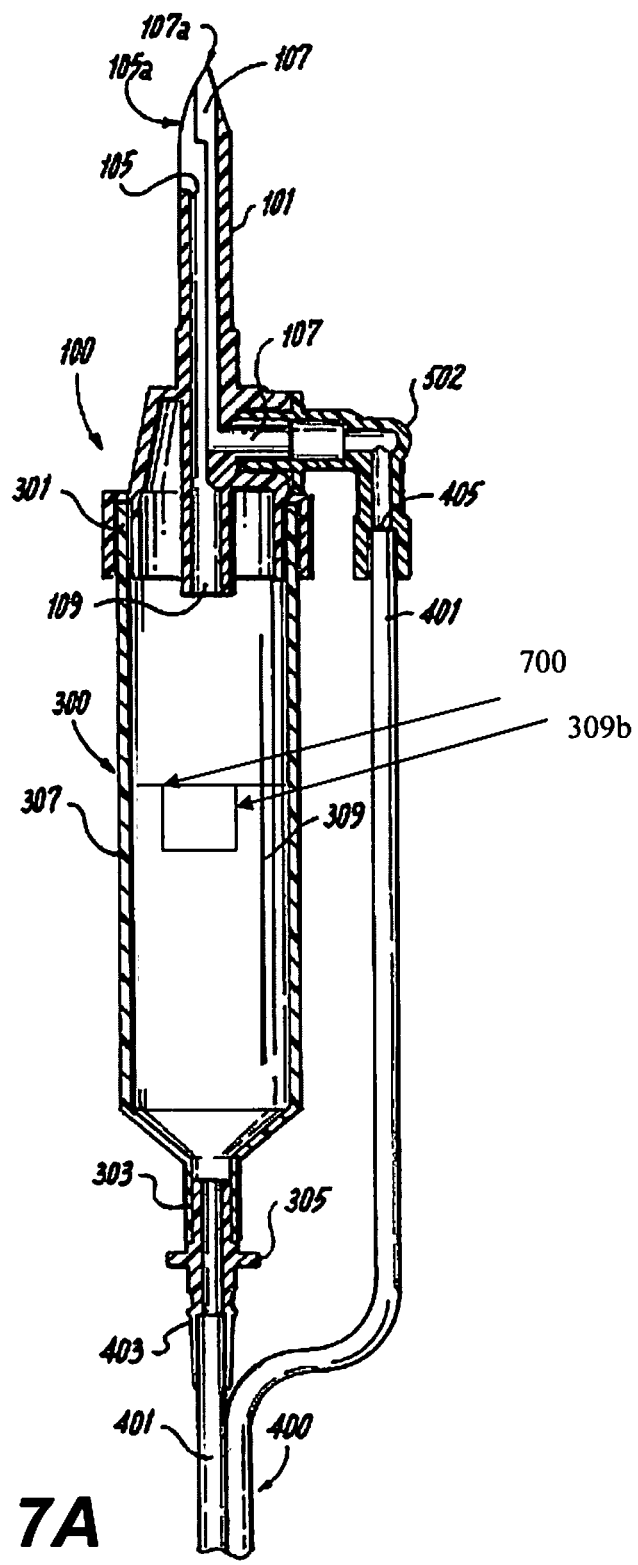
FIGS. 7A and 7B are cross-sectional views of a drip chamber and a flow indicator, in accordance with the present disclosure.
Figure 7B:
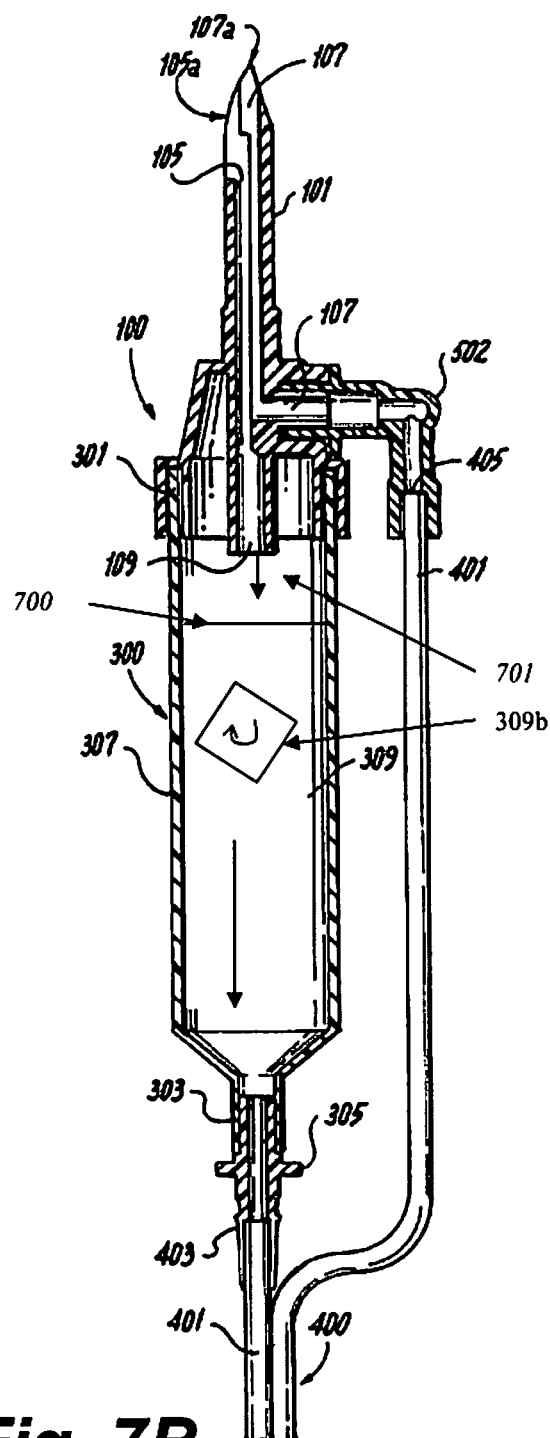

An alternative arrangement of a flow indicator 309a is depicted in FIGS. 7A and 7B. As shown in FIGS. 7A and 7B, the flow indicator 309a is generally in the shape of a cube, though other geometric shapes may be employed without departing from the scope of the present disclosure. The cube shape may be advantageous by eliminating the possibility of the flow indicator 309a occluding the bottom portion 303 of the drip chamber 300 when the system 1000 is initially primed with the fluid. The flow indicator 309a has a density related to the cooling fluid such that when fluid is not flowing through the drip container 300 the flow indicator 309a floats to the upper surface 700 of the fluid in the drip container 300 as shown in FIG. 7A and when fluid is flowing through the drip container 300 the flow indicator 309a partially submerges beneath the surface 700 and may also rotate to provide visual indicia of fluid flow as shown in FIG. 7B.

The tubing system 400 may include one or more return fluid flow indicators disposed thereon to indicate that a fluid is returning from the medical device to the reservoir 200 through tubing system 400. Examples of such return flow indicator include bubble indicators and traps, Venturi-style indicators, Hall-effect fluid flow indicators, and the like. Indicators, such as bubble indicators and venturi devices, also have the dual purpose of removing any gas which may have entered the system or vapor from the liquid flow to prevent disruption in the flow. Other fluid flow indicators may also be employed to measure fluid velocity, pressure, or volumetric flow rate. Examples of the fluid flow indicators are currently sold by Introtek International under the name BDC and BER Ultrasonic Clamp-on Air Bubble, Air-in-line & Liquid level Detection Systems as well as the Drip Chamber Ultrasonic Liquid Level Sensors.

FIG. 8 illustrates numerous locations where flow indicators 309b and thermocouples 202, as described above, may be employed within system 1000. The flow indicators 309b are flow sensors that detect flow of a fluid between portions of the flow indicators 309b. The flow indicators 309b and thermocouples 202 may be attached to various portions of the system 1000 and may be attached to devices (not shown) that provide audible and/or visual indicia of fluid flow within the system 1000. Further, the devices themselves may provide audible and/or visual indicia when fluid is not flowing within portions of the system 1000, e.g. when a tube is kinked or blocked.

Referring now to FIGS. 1 and 2, the tubing system 400 includes one or more tubes 401 that allow a fluid to flow from the reservoir connector assembly 100, through an energy delivery device (not shown) such as an ablation needle or catheter or an energy source, and back to the reservoir connector assembly 100. The tubing system 400 may include a first end 403 and a second end 405.

In the illustrated embodiment, the first end 403 is in fluid communication with the outflow port 109, either indirectly through the bottom portion 303 of drip chamber 300 or by direct connection to outflow port 109, and is configured to allow fluid to flow into tubing system 400. The second end 405 is in fluid communication with the return port 103, and is configured to allow fluid to return to the reservoir 200 through the second lumen 107.

Tubing system 400 may also include one or more thermal diffusion devices 407 configured to draw heat from the fluid and diffuse the heat to the ambient environment. As shown in FIG. 1, the thermal diffusion device 407 includes a series of fins 409 in contact with the tube 401 returning from a medical device. A fan may be employed to direct airflow over the fins and increase the cooling effect. While shown connected to the tube 401, a thermal diffusion device 409 could also or alternatively be employed on the reservoir 200. A further alternative could employ passing the tube 401 returning from the medical device through a reservoir containing cold water or ice water in order to further draw heat out of the fluid flowing through the tubes 401.

The system 1000 may further include an elbow member 500 connected to the second end 405 of the tubing system 400 as shown in FIGS. 5A-C. The second end 405 of the tubing system 400 in fluid communication with the return port 103 through the elbow member 500.

The elbow member 500 may include a body 501 defining a lumen 503, an inflow port 505 in fluid communication with the lumen 503, and an outflow port 507 in fluid communication with the lumen 503. The inflow port 505 is configured to connect to a return section or second end 405 of a tubing system 400, and the outflow port 507 is configured to connect to or accept the return port 103 of the reservoir connection assembly 100.

The elbow member 500 may further have a flange 509 disposed around the outflow port 507 to ensure proper alignment of the elbow 500 with the reservoir connection assembly 100 as shown in FIGS. 4A and 4B. For example, as shown, flange 509 has a tombstone shape with a flat portion on a bottom portion thereof to allowing for connection with return port 103 in only one orientation of the elbow 500.

In at least some embodiments, the elbow 500 is formed of molded plastic. The elbow 500 may be injection molded, blow molded, or formed in any other suitable manner known in the art. The elbow 500 may be made of one solid piece or a conglomeration of subparts.

In one embodiment, one or more pumps may be used to control fluid flow through the cooling system 1000. Referring to FIG. 6, a pump 600 may be connected to the tubing system 400 to pressurize a fluid in the tubing 401. While any pump known in the art can be used, as shown FIG. 6, the type of pump 600 used is a peristaltic pump which applies pressure to compress the outside of a pump tubing 602 forcing fluid downstream towards the medical device. The pump tubing 602 may be made of a thicker gauge of the same material or a different material than the tubing 401, thus allowing it to withstand the repetitive stresses of the peristaltic pump for the duration of a medical procedure. Connectors 604 may be used to fluidly connect the pump tubing 602 to the tubing 401. Further, a protective slip cover 606 may alternatively be used to protect either the pump tubing 602, or the tubing 401, if no pump tubing 602 is utilized. Though described herein with respect to a peristaltic pump, any device suitable to create a pressure to advance fluid through the tubing 401 in the cooling system 1000 may be used.

As an alternative to using a peristaltic pump 600, the entire system 1000 may rely on gravity and the change in density of the fluid as it is heated to allow the fluid to circulate through the system 1000. For example, as water heats, its density at 1 atm (sea level) decreases from about 62.4 lb/ft$^3$ at 60° F. to about 60 lb/ft$^3$ at 212° F. This difference in density may in some circumstances promote sufficient circulation of the fluid through the system 1000 to maintain proper cooling of the medical device.

The fluid used in cooling system 1000 may be any suitable liquid such as saline solution, de-ionized water, sugar water, and combinations thereof, or the like. For example, the reservoir 200 may be a saline bag traditionally used in medicine.

In use, the tubing system 400 is connected to a medical device (not shown) to cool the medical device. The medical device may have cooling lumens such as those found in microwave ablation probes and microwave ablation catheters. The tubing system 400 connects to an inflow port of the medical device allowing cooling fluid to flow through the lumens of the medical device to and flow out of an outflow port on the medical device. The cooling fluid may pumped from the reservoir 200 through the medical device, as described above, or alternatively, the cooling fluid may be gravity fed to the medical device. The cooling system 1000 may include the reservoir connection assembly 100 and the drip chamber 300 in fluid communication with the tubing system 400, as described above. The cooling fluid flows from the reservoir 200 through the reservoir connection assembly 100, drip chamber 300, and the tubing system 400 into the inflow port of the medical device. The fluid returns to the reservoir 200 flowing from the outflow port of the medical device through tubing system 400, the return port 103, and the second lumen 107 of reservoir connection assembly 100. The fluid extracts or absorbs heat from the medical device to cool the device. As the fluid is traveling through system 1000, it releases some heat into the environment surrounding the tubing system 400. If thermal diffusion devices 407 are connected to the system 1000, heat may be released from the fluid more efficiently, allowing for a reduced operating temperature of the system 1000.

Temperatures maintained in the system 1000 and the energy delivery device should be within a range to avoid injury to the patient and adequate to allow flow through the system. For example, the temperature should be below approximately 113° F. to avoid injury to the patient and above the freezing temperature of the fluid. Pressures and flow rates within the system 1000 and the components thereof may be varied through variations in pump speed, and through design of the system 1000 and the components thereof.

Some example performance parameters include:

|  | Pump | Microwave Needle Ablation Probe | Microwave Ablation Catheter |
| --- | --- | --- | --- |
| Pressure | 35-45 psi Up to 60 psi | 45-55 psi | 50-70 psi |
| Flow Rate | 4.8-6.1 in$^3$/min | 4.2-5.5 in$^3$/min | 1.4-1.8 in$^3$/min |

One of the advantages of the cooling system 1000 described herein is that it can employ standard sterile saline bags as the fluid reservoir, which eliminates the need for a specialized fluid source. Further the system 1000 recirculates fluid as opposed to simply dumping the cooling fluid after one pass through the medical device, thereby conserving cooling fluid and eliminating the need for a collection bucket or bag.

Methods are also disclosed herein. In an embodiment, a method may include providing a saline bag or other fluid reservoir and a saline bag elongate member having multiple lumens defined therein. The saline bag elongate member includes at least one return port connected to at least one of the lumens. The method may also include providing a drip container such as the drip container 300 disclosed herein.

The method may further include providing an elbow 500 as disclosed herein. The method further includes connecting the elbow 500 to the return port of the saline bag elongate member to allow fluid flow to return into the saline bag through the return port. The method also includes the step of connecting a return portion of the tubing system 400 to the elbow 500.

Also disclosed is a method for recirculating a cooling fluid for use with an energy delivery device. The method includes providing an energy delivery device, providing a recirculating cooling system connected to the energy delivery device, and recirculating a fluid through the cooling system and energy delivery device to maintain the energy delivery device at a desired temperature or within a desired temperature range to prevent undesired damage to tissue. The desired temperature range may include an upper limit corresponding to a temperature above which tissue is damaged and a lower limit below which the fluid will not flow within the system. The flow rate of fluid within the system may be adjusted as the temperature approaches the upper limit or the lower limit. For example, when the temperature approaches the upper limit the flow rate may be increased to increase the cooling of the medical device. The system may include visual or audible indicia when the temperature approaches the upper or lower limit.

It should be understood that the foregoing description is only illustrative of the present disclosure. Various alternatives and modifications can be devised by those skilled in the art without departing from the disclosure. Accordingly, the present disclosure is intended to embrace all such alternatives, modifications, and variances. The embodiments described with reference to the attached drawing figs. are presented only to demonstrate certain examples of the disclosure. Other elements, steps, methods, and techniques that are insubstantially different from those described above and/or in the appended claims are also intended to be within the scope of the disclosure.

What is claimed is:

1. An medical device cooling system, the system comprising:
    a reservoir connector assembly connectable to a reservoir and including:
        an elongate member configured to extend into the reservoir past a connection port of the reservoir, the elongate member including a first lumen and a second lumen defined therethrough, each lumen in fluid communication with the reservoir;
        at least one outflow port in fluid communication with the first lumen; and
        at least one return port in fluid communication with the second lumen; and
    a tubing system comprising a first end and a second end, the first end connected to and in fluid communication with the outflow port, the second end connected to and in fluid communication with the return port, the tubing system configured to cool a medical device.

2. The system of claim 1, further comprising a pump configured to pressurize a fluid in the tubing system to create a fluid flow in the tubing system.

3. The system of claim 2, wherein the pump is a peristaltic pump.

4. The system of claim 1, wherein the elongate member further includes a third lumen and a fourth lumen in fluid communication with the reservoir and the at least one outflow port.

5. The system of claim 1, further including at least one drip chamber connected downstream of the outflow port.

6. The system of claim 5, wherein the drip chamber includes a fluid flow indicator.

7. The system of claim 6, wherein the fluid flow indicator is a rotating cylinder.

8. The system of claim 6, wherein the fluid flow indicator is a semi-buoyant spinning cube.

9. The system of claim 1, wherein the tubing system includes at least one thermal diffusion device configured to draw heat from the fluid and diffuse the heat to an ambient environment.

10. The system of claim 1, wherein the reservoir is a saline bag.

11. The system of claim 1, further including an elbow member, wherein the second end of the tubing system is connected to the elbow member and is in fluid communication with the return port through the elbow member.

12. A fluid return elbow for use with a medical device cooling system, the elbow comprising:
a body defining a lumen;
an inflow port in fluid communication with the lumen, the inflow port configured to connect to a return section of a fluid tubing system;
an outflow port in fluid communication with the lumen, the outflow port configured to connect to a return port of a reservoir connection assembly; and
a flange disposed around the outflow port configured to ensure proper alignment of the elbow with the reservoir connection assembly.

13. The elbow of claim 12, wherein the inflow port is configured to connect to tubing of a cooling system for a medical device, and wherein the outflow port is configured to connect to a return port of an elongate member inserted into a saline bag.

14. A system for cooling a medical ablation device, the system comprising:
a fluid reservoir configured to hold a cooling fluid;
a tubing system connected to and in fluid communication with the fluid reservoir;
a pump connected to the tubing system and configured to induce the cooling fluid to flow from the reservoir through the tubing system;
the medical ablation device connected to the tubing system configured to allow the cooling fluid to flow through the medical ablation device and draw heat therefrom, wherein the tubing system is connected to the fluid reservoir such that the fluid is returned to the fluid reservoir and reused; and
a fluid flow indicator disposed within a flow of cooling fluid from the fluid reservoir to the pump and configured to provide local indicia of the flow of cooling fluid from the fluid reservoir to the pump.

15. The system of claim 14, wherein the system further includes at least one thermal diffusion device to facilitate thermal diffusion from the cooling fluid disposed in the system.

16. The system of claim 14, wherein the fluid flow indicator is selected from the group of fluid flow indicators consisting of bubble indicators, venturi devices, drip chamber indicators, float type indicators, hall-effect indicators, and electromagnetic indicators.

17. The system of claim 14, wherein the tubing system includes a first tube and a second tube, the first tube connected to and in fluid communication with an outflow port of the fluid reservoir and an inflow port of the medical ablation device, the second tube connected to and in fluid communication with an exit port of the medical ablation device and a return port of the fluid reservoir.

18. The system of claim 14, further comprising a drip container connected to and in fluid communication with an outflow port of the fluid reservoir and the tubing system.

19. The system of claim 14, further comprising an elbow connected to and in fluid communication with a return port of the fluid reservoir and the tubing system.

20. The elbow of claim 12, wherein the flange defines a tombstone shape configured to ensure proper alignment of the elbow with the reservoir connection assembly.

21. The system of claim 1, wherein the elongate member is configured to extend into the reservoir into a main volume of the reservoir.

* * * * *